(12) United States Patent
Sa et al.

(10) Patent No.: US 11,020,071 B2
(45) Date of Patent: Jun. 1, 2021

(54) X-RAY COMPUTED TOMOGRAPHY APPARATUS WITH SCANNER FUNCTION

(71) Applicant: Ray Co., Ltd., Gyeonggi-do (KR)

(72) Inventors: Yong Jae Sa, Gyeonggi-do (KR); Sang Chul Lee, Gyeonggi-do (KR)

(73) Assignee: Ray Co., Ltd., Gyeonggi-do (KR)

( * ) Notice: Subject to any disclaimer, the term of this patent is extended or adjusted under 35 U.S.C. 154(b) by 28 days.

(21) Appl. No.: 16/629,548

(22) PCT Filed: Jul. 26, 2017

(86) PCT No.: PCT/KR2017/008033
§ 371 (c)(1),
(2) Date: Jan. 8, 2020

(87) PCT Pub. No.: WO2019/013377
PCT Pub. Date: Jan. 17, 2019

(65) Prior Publication Data
US 2021/0030382 A1    Feb. 4, 2021

(30) Foreign Application Priority Data

Jul. 11, 2017 (KR) .......................... 10-2017-0087628

(51) Int. Cl.
*A61B 6/00* (2006.01)
*A61B 6/03* (2006.01)
(Continued)

(52) U.S. Cl.
CPC ............ *A61B 6/4417* (2013.01); *A61B 6/032* (2013.01); *A61B 6/0407* (2013.01);
(Continued)

(58) Field of Classification Search
CPC ..... A61B 6/4417; A61B 6/0487; A61B 6/032; A61B 6/0407; A61B 6/42; A61B 6/4435;
(Continued)

(56) References Cited

U.S. PATENT DOCUMENTS

| 6,188,747 B1 | 2/2001 | Geus et al. | |
|---|---|---|---|
| 2014/0177808 A1 | 6/2014 | Charette et al. | |
| 2015/0010126 A1* | 1/2015 | Rotondo | A61B 6/06 378/19 |

FOREIGN PATENT DOCUMENTS

| KR | 1020070107574 A | 11/2007 |
|---|---|---|
| KR | 1020100055972 A | 5/2010 |
| KR | 1020120027262 A | 3/2012 |

* cited by examiner

*Primary Examiner* — Courtney D Thomas

(57) ABSTRACT

An X-ray computed tomography apparatus with a scanner function includes a vertical frame, a patient support arm provided below the vertical frame, a horizontal support arm extending horizontally from a top portion of the vertical frame, a rotary arm drive unit provided at an end of the horizontal support arm, a horizontal rotation arm provided horizontally below the rotary arm drive unit to rotate 360 degrees, a general CT imaging X-ray source provided at one end of the horizontal rotation arm, and an X-ray detector provided at the other end of the horizontal rotation arm to face the general CT imaging X-ray source. A micro CT imaging X-ray source is provided on the vertical frame, a rotary table for seating and rotating an object to be imaged is provided above the patient support arm, and the X-ray detector is composed of a common X-ray detector.

11 Claims, 9 Drawing Sheets

(51) Int. Cl.
   *G01N 23/046*   (2018.01)
   *A61B 6/04*   (2006.01)
(52) U.S. Cl.
   CPC .......... *A61B 6/0487* (2020.08); *A61B 6/4007* (2013.01); *A61B 6/42* (2013.01); *A61B 6/4435* (2013.01); *A61B 6/4452* (2013.01); *A61B 6/4458* (2013.01); *G01N 23/046* (2013.01); *G01N 2223/30* (2013.01); *G01N 2223/419* (2013.01)
(58) Field of Classification Search
   CPC ....... A61B 6/4452; A61B 6/4458; A61B 6/40; A61B 6/4275; A61B 6/4007; G01N 23/046; G01N 2223/30; G01N 2223/419
   See application file for complete search history.

[FIG. 1]    Prior Art
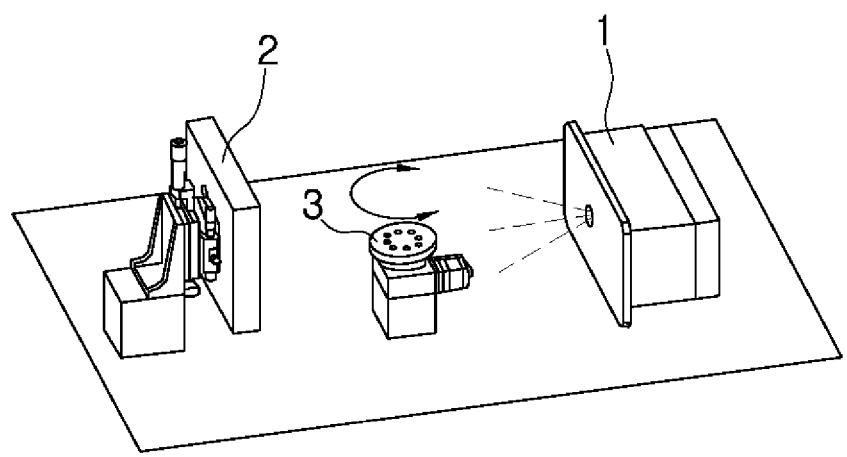

[FIG. 2]　Prior Art
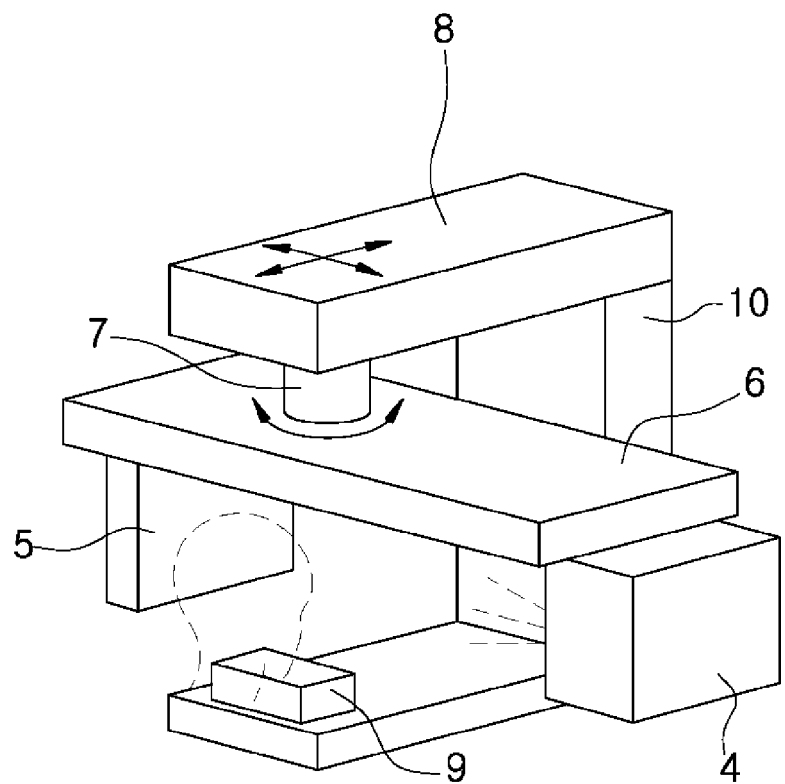

[FIG. 3]
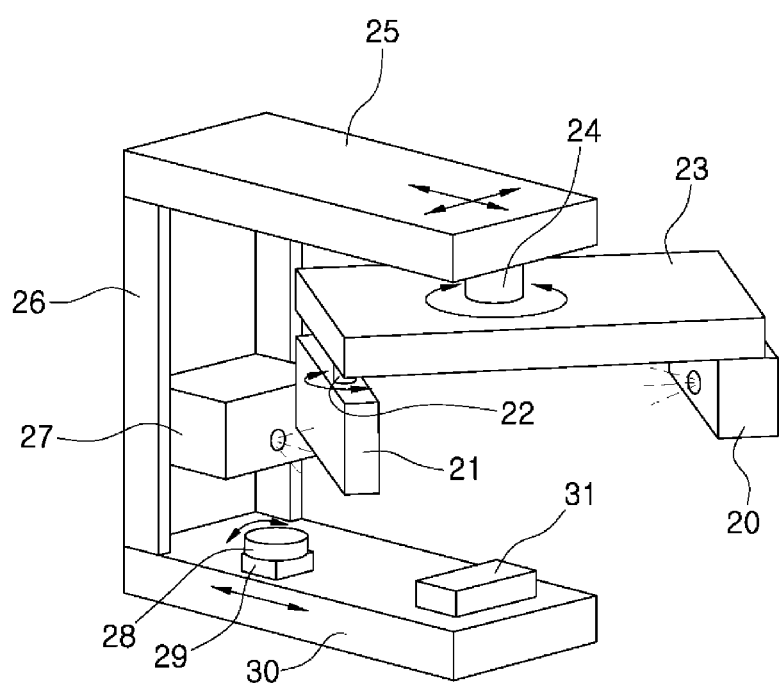

[FIG. 4]
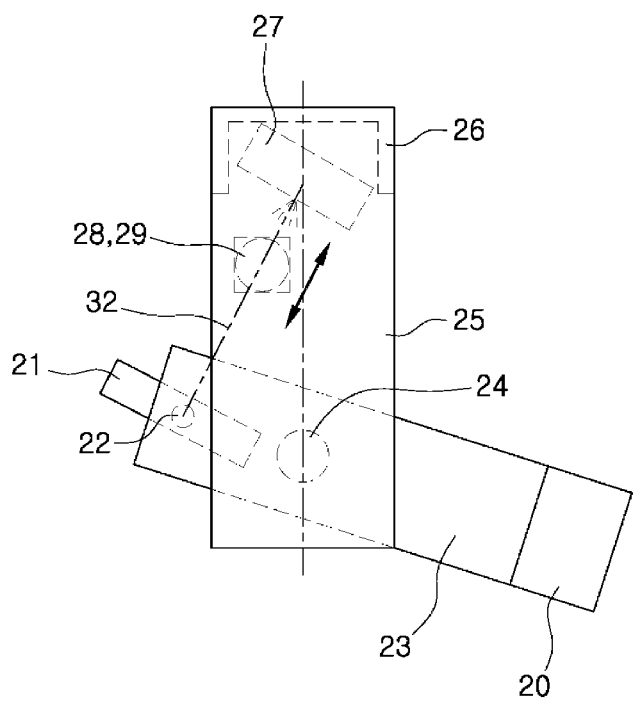

[FIG. 5]
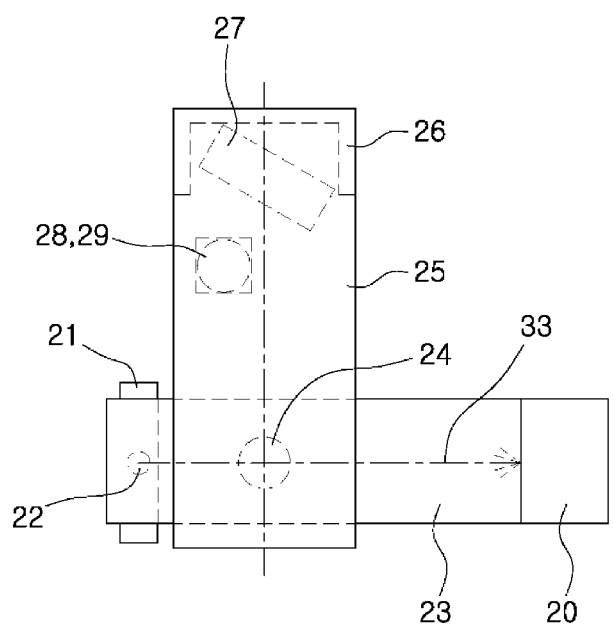

[FIG. 6]
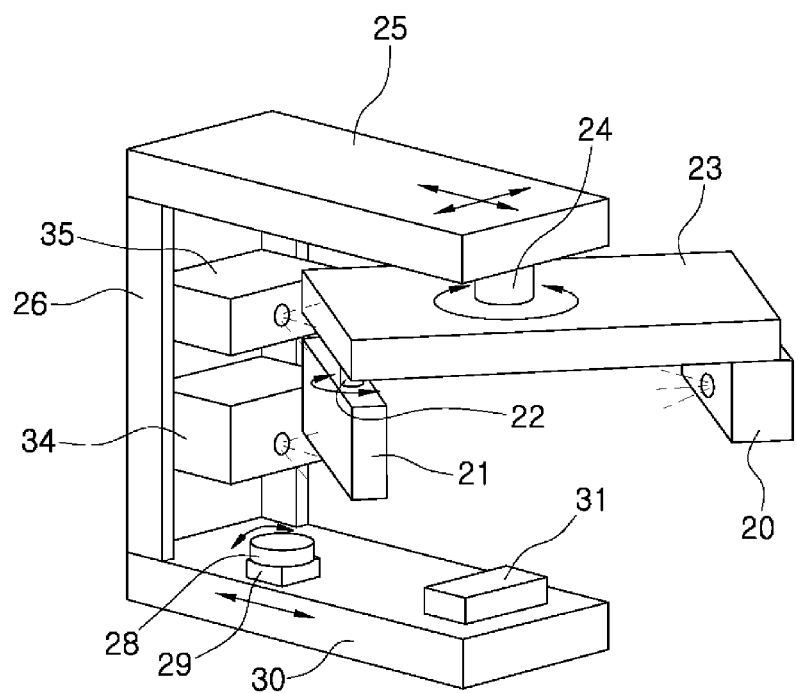

[FIG. 7]
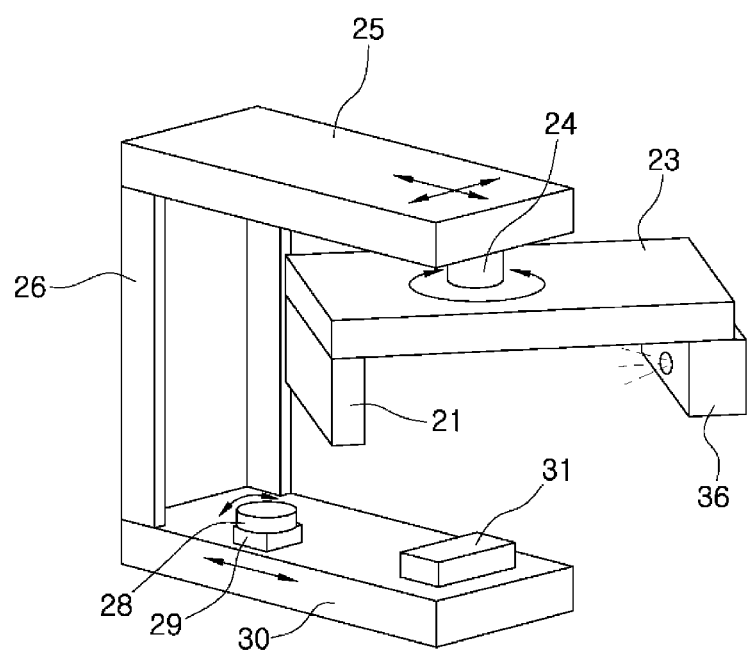

[FIG. 8]
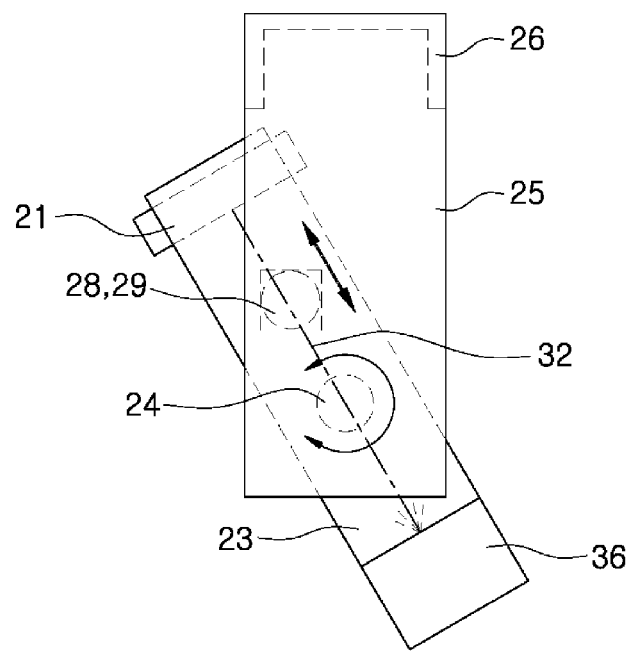

[FIG. 9]
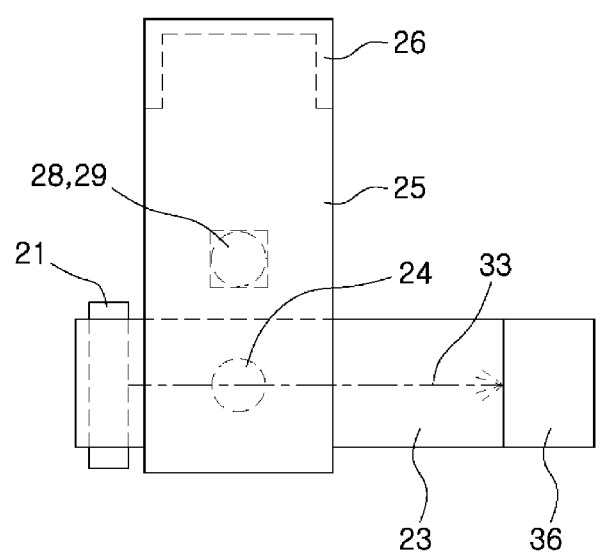

X-RAY COMPUTED TOMOGRAPHY APPARATUS WITH SCANNER FUNCTION

CROSS-REFERENCE TO RELATED PATENT APPLICATIONS

This application is a United States national phase application based on PCT/KR2017/008033 filed Jul. 26, 2017 which claims the benefit of Korean Patent Application No. 10-2017-0087628 dated Jul. 11, 2017. The disclosure of the above patent application is hereby incorporated herein by reference in its entirety.

TECHNICAL FIELD

The present invention relates to an X-ray computed tomography apparatus used in hospitals or the like and, more particularly, to an X-ray computed tomography apparatus with a scanner function, which is configured to perform both a micro CT imaging operation of imaging an impression body, a model or the like at a high resolution and a general CT imaging operation of imaging a part of a human body.

BACKGROUND ART

A computed tomography (hereinafter simply referred to as "CT") includes a micro CT for imaging a small object at a high resolution and a CT for imaging a part of a body of a patient (hereinafter referred to as "general CT" so as to be distinguished from the micro CT).

The micro CT is used for the purpose of imaging a small object such as an impression body or a model at a high resolution, whereas the general CT is used for the purpose of imaging a part of a body of a patient, such as the oral cavity or the head of a patient.

FIG. 1 schematically shows the above-mentioned micro CT, and FIG. 2 schematically shows the structure of the general CT.

First, as shown in FIG. 1, the micro CT includes a micro CT X-ray source 1 for generating an X-ray, and an X-ray detector 2 installed to face the X-ray source 1 in order to detect a transmission value of the X-ray radiated from the X-ray source 1.

A rotary table 3 for seating and rotating an object to be imaged is provided between the micro CT X-ray source 1 and the micro CT X-ray detector 2.

The micro CT X-ray source 1, the rotary table 3 and the micro CT X-ray detector 3 are arranged along a straight line.

In the micro CT shown in FIG. 1, while seating a target object on the rotary table 3 and rotating the rotary table 3, an X-ray is irradiated from the micro CT X-ray source 1 and a transmission value is detected by the micro CT X-ray detector 2.

Typically, an X-ray is generated by applying a high voltage to between a cathode (sometimes a filament) and an anode provided inside a tube of an X-ray source, accelerating electrons emitted from the anode, and causing the electrons to collide with an anode as a target.

The above-mentioned micro CT is not used to image a body of a patient, but is used to image a small object such as an impression body or a model at a high resolution.

Meanwhile, FIG. 2 schematically shows a general CT for imaging a body of a patient such as the oral cavity or the head of a patient.

As shown in FIG. 2, in a general CT for imaging the oral cavity or the entire head of a patient, a general CT X-ray source 4 and a general CT X-ray detector 5 for detecting the transmission value of the X-ray irradiated from the X-ray source 4 are provided under a horizontal rotation arm 6 so as to face each other.

The horizontal rotation arm 6 is driven by a rotary drive unit 7 provided above the horizontal rotation arm 6. The horizontal rotation arm 6 is provided so that it can be moved in front-rear and left-right directions and rotated by the rotary drive unit 7.

The upper portion of the horizontal rotation arm 6 is provided with a horizontal support arm 8, which is connected to a vertical frame 10. The lower portion of the horizontal rotation arm 6 is provided with a jaw support portion 9 for supporting the head of a patient.

In order to perform imaging by the above-mentioned general CT, the horizontal rotation arm 6 is rotated in a state in which the head of the patient is supported by the jaw support portion 9. Then, CT imaging is performed as the general CT X-ray source 4 and the general CT X-ray detector 5 rotate 360 degrees around the head of the patient.

The general CT X-ray detector 5 detects the transmission value of the X-ray. The analog signal thus collected is converted into a digital signal, which is processed in a computer to obtain a three-dimensional image. The image information thus obtained is used for disease diagnosis or simulated surgery for the oral cavity or the entire head portion.

The general CT described above is used to image a part of a body of a patient, such as the oral cavity or the head, unlike the micro CT for imaging a small object.

However, in a dental clinic or the like, it is necessary to acquire three-dimensional data of an impression body or a model at a high resolution. Accordingly, a combination of general CT and micro CT, or a combination of general CT and high-resolution 3D scanner has to be provided in the dental clinic or the like. This poses a problem in that the purchase cost is increased and the installation space of the equipment is increased.

SUMMARY

With the aforementioned problems in view, it is an object of the present invention to provide an X-ray computed tomography apparatus capable of performing both a micro CT imaging operation of imaging a small object at a high resolution and a general CT imaging operation of imaging a part of a body of a patient.

Another object of the present invention is to provide an X-ray computed tomography apparatus capable of reducing equipment purchase cost and installation space.

A further object of the present invention is to provide an X-ray computed tomography apparatus capable of performing both a micro CT imaging operation and a general CT imaging operation without significantly increasing costs.

According to one aspect of the present invention, there is provided an X-ray computed tomography apparatus with a scanner function, including: a vertical frame; a patient support arm provided below the vertical frame; a horizontal support arm extending horizontally from a top portion of the vertical frame; a rotary arm drive unit provided at an end of the horizontal support arm; a horizontal rotation arm provided horizontally below the rotary arm drive unit to rotate 360 degrees; a general CT imaging X-ray source provided at one end of the horizontal rotation arm; and an X-ray detector provided at the other end of the horizontal rotation arm to face the general CT imaging X-ray source, wherein a micro CT imaging X-ray source is further provided on the vertical frame, a rotary table for seating and rotating an object to be imaged is further provided above the patient support arm, and the X-ray detector is composed of a common X-ray detector capable of being rotated by an X-ray detector drive unit, so that the apparatus can perform both a micro CT imaging operation and a general CT imaging operation.

A rotary table drive unit for rotating the rotary table may be provided below the rotary table.

The rotary table drive unit may be provided so as to be movable along a rail provided on the patient support arm.

The rotary table or the rotary table drive unit may be detachably provided on an upper surface of the patient support arm.

The micro CT imaging X-ray source may be provided to be able to move up and down and rotate at a predetermined angle in a horizontal direction.

When performing the micro CT imaging operation, the micro CT imaging X-ray source and the common X-ray detector may be rotated at a predetermined angle, the centers of the micro CT imaging X-ray source and the rotary table may be placed on a line, and then the micro CT imaging X-ray source and the common X-ray detector may be allowed to face each other.

A first X-ray source and a second X-ray source for performing the micro CT imaging operation by irradiating X-rays having different focuses may be provided on the vertical frame.

According to another aspect of the present invention, there is provided an X-ray computed tomography apparatus with a scanner function, including: a vertical frame; a patient support arm provided below the vertical frame; a horizontal support arm extending horizontally from a top portion of the vertical frame; a rotary arm drive unit provided at an end of the horizontal support arm; a horizontal rotation arm provided horizontally below the rotary arm drive unit to rotate 360 degrees; an X-ray source provided at one end of the horizontal rotation arm; and an X-ray detector provided at the other end of the horizontal rotation arm to face the X-ray source, wherein the X-ray source is composed of a dual focus type X-ray source capable of emitting both a micro CT imaging X-ray and a general CT imaging X-ray from one tube, so that the apparatus can perform both a micro CT imaging operation and a general CT imaging operation.

According to the X-ray computed tomography apparatus of the present invention, it is possible to perform both a micro CT imaging operation of imaging a small object at a high resolution and a general CT imaging operation of imaging a part of a body of a patient.

Furthermore, it is possible to reduce equipment purchase cost and installation space, because both the micro CT imaging operation and the general CT imaging operation can be performed in one X-ray computed tomography apparatus.

In addition, it is possible to perform both the micro CT imaging operation and the general CT imaging operation without significantly increasing costs.

BRIEF DESCRIPTION OF THE DRAWINGS

FIG. 1 is a perspective view schematically showing a conventional micro CT apparatus.

FIG. 2 is a perspective view schematically showing a conventional general CT apparatus.

FIG. 3 is a perspective view schematically showing an X-ray CT apparatus according to a first embodiment of the present invention.

FIG. 4 is a plan view for explaining a case where a micro CT imaging operation is performed using the X-ray CT apparatus according to the first embodiment of the present invention.

FIG. 5 is a plan view for explaining a case where a general CT imaging operation is performed using the X-ray CT apparatus according to the first embodiment of the present invention.

FIG. 6 is a perspective view schematically showing an X-ray CT apparatus according to a second embodiment of the present invention.

FIG. 7 is a perspective view schematically showing an X-ray CT apparatus according to a third embodiment of the present invention.

FIG. 8 is a plan view for explaining a case where a micro CT imaging operation is performed using the X-ray CT apparatus according to the third embodiment of the present invention.

FIG. 9 is a plan view for explaining a case where a general CT imaging operation is performed using the X-ray CT apparatus according to the third embodiment of the present invention.

DETAILED DESCRIPTION

Preferred embodiments of the present invention will now be described in detail with reference to the accompanying drawings.

First Embodiment

FIGS. 3 to 5 show an X-ray computed tomography (CT) apparatus according to a first embodiment of the present invention. Referring to FIG. 3, the X-ray CT apparatus with a scanner function according to the first embodiment of the present invention includes: a vertical frame 26; a patient support arm 30 provided below the vertical frame 26; a horizontal support arm 25 extending horizontally from a top portion of the vertical frame 26; a rotary arm drive unit 24 provided at an end of the horizontal support arm 25; a horizontal rotation arm 23 provided horizontally below the rotary arm drive unit 24 to rotate 360 degrees; a general CT imaging X-ray source 20 provided at one end of the horizontal rotation arm 23; and an X-ray detector provided at the other end of the horizontal rotation arm 23 to face the general CT imaging X-ray source 20, wherein a micro CT imaging X-ray source 27 is further provided on the vertical frame 26, a rotary table 28 for seating and rotating an object to be imaged is further provided above the patient support arm 30, and the X-ray detector is composed of a common X-ray detector 21 capable of being rotated by an X-ray detector drive unit 22.

That is, the X-ray CT apparatus according to the present embodiment includes both the micro CT imaging X-ray source 27 and the general CT imaging X-ray source 20.

According to the above structure, it is possible to perform both a micro CT imaging operation of imaging an object such as an impression body, a model or the like at a high resolution and a general CT imaging operation of imaging a part of a body of a patient.

In addition, both the micro CT imaging operation and the general CT imaging operation can be performed with only one expensive X-ray detector, which makes it possible to manufacture the X-ray CT apparatus without increasing costs.

A rotary table drive unit 29 for rotating the rotary table 28 is provided below the rotary table 28 on which an object to be imaged is seated.

The rotary table 28 and the rotary table drive unit 29 may be fixedly installed, or may be configured to be movable along a rail to change a magnification during the micro CT imaging operation. The rotary table 28 may be detachably provided on the upper surface of the rotary table drive unit 29. In addition, the rotary table 28 may be fixed to the upper surface of the rotary table drive unit 29, and the rotary table drive unit 29 may be detachably provided on the upper surface of the patient support arm 30.

In addition, the micro CT imaging X-ray source 27 is provided so as to be movable up and down and rotatable at a predetermined angle in a horizontal direction.

According to the above structure, the micro CT imaging operation can be performed while adjusting the position of the micro CT imaging X-ray source 27.

Hereinafter, a process of performing a micro CT imaging operation and a general CT imaging operation using the X-ray CT apparatus according to the first embodiment of the present invention will be described.

First, when performing the micro CT imaging operation, as shown in FIG. 4, the object to be imaged is seated on the rotary table 28. Then, the common X-ray detector 21 provided at one end of the horizontal rotation arm 23 is rotated to align the micro CT imaging X-ray source 27. In other words, the horizontal rotation arm 23 is rotated by the rotary arm drive unit 24, and the common X-ray detector 21 is rotated by the X-ray detector drive unit 22. At this time, the centers of the micro CT imaging X-ray source 27 and the rotary table 28 are aligned with each other, and the X-ray source 27 and the common X-ray detector 21 are caused to face each other. In FIG. 4, reference numeral 32 denotes an X-ray center axis during the micro CT imaging operation.

An X-ray is irradiated from the micro CT imaging X-ray source 27 while rotating the rotary table 28. Then, the common X-ray detector 21 detects the X-ray passing through the object and transmits a detection signal to the computer.

Next, a process of performing a general CT imaging operation using the X-ray CT apparatus according to the first embodiment of the present invention will be described.

In the case of performing the general CT imaging operation, a part of the body of the patient is placed on the patient support arm 30. Then, as shown in FIG. 5, the general CT imaging X-ray source 20 and the common X-ray detector 21 are caused to face each other. In FIG. 5, reference numeral 33 denotes an X-ray center axis during the general CT imaging operation.

In this state, an X-ray is irradiated from the general CT imaging X-ray source 20 while rotating the horizontal rotation arm 23 around the head of the patient. Then, the common X-ray detector 21 detects the X-ray transmitted through a part of the human body and transmits a detection signal to the computer.

According to the present invention, it is possible to perform both the micro CT imaging operation and the general CT imaging operation using one X-ray CT apparatus.

In particular, the micro CT imaging operation and the general CT imaging operation can be performed using only one expensive X-ray detector, with making it possible to manufacture the X-ray CT apparatus at a relatively low cost.

In addition, since both the micro CT imaging operation and the general CT imaging operation can be performed using one X-ray CT apparatus, it is possible to reduce the equipment purchase cost and enhance the space utilization.

Second Embodiment

FIG. 6 shows an X-ray CT apparatus according to a second embodiment of the present invention. The X-ray CT apparatus according to the second embodiment of the present invention includes two micro CT imaging X-ray sources, each of which is employed in the first embodiment.

That is, as shown in FIG. 6, a first X-ray source 34 and a second X-ray source 35 for performing a micro CT imaging operation by irradiating X-rays having different focuses are provided on the vertical frame 10 employed in the first embodiment.

According to the second embodiment of the present invention, there is an advantage that it is possible to perform a micro CT imaging for various objects.

Other matters are the same as those of the first embodiment described above, and the redundant description thereof will be omitted.

Third Embodiment

FIGS. 7 to 9 show an X-ray computed tomography (CT) apparatus according to a third embodiment of the present invention. Referring to FIG. 7, the X-ray CT apparatus with a scanner function according to the third embodiment of the present invention includes: a vertical frame 26; a patient support arm 30 provided below the vertical frame 26; a horizontal support arm 25 extending horizontally from a top portion of the vertical frame 26; a rotary arm drive unit 24 provided at an end of the horizontal support arm 25; a horizontal rotation arm 23 provided horizontally below the rotary arm drive unit 24 to rotate 360 degrees; an X-ray source 20 provided at one end of the horizontal rotation arm 23; and an X-ray detector provided at the other end of the horizontal rotation arm 23 to face the X-ray source, wherein the X-ray source is composed of a dual focus type X-ray source 36 capable of emitting both a micro CT imaging X-ray and a general CT imaging X-ray from one tube.

That is, the dual focus type X-ray source 36 includes two X-ray sources provided in an X-ray tube and capable of emitting X-rays having different focuses.

According to the third embodiment of the present invention, both a micro CT imaging operation and a general CT imaging operation can be performed using only one X-ray tube and one X-ray detector.

First, when performing a micro CT imaging operation, as shown in FIG. 8, the horizontal rotation arm 24 is rotated by the rotary arm drive unit 24, and the horizontal support arm 25 is moved in front-rear and left-right directions so that the center of the dual focus type X-ray source 36 provided at one end of the horizontal rotation arm 23 coincides with the center of the rotary table 28.

Then, the dual focus type X-ray source 36 and the common X-ray detector 21 are caused to face each other. At this time, the horizontal rotation arm 23 may be moved in front-rear and left-right directions in order to adjust a magnification. It is also possible to adjust the magnification by moving the rotary table 28 in front-rear and left-right directions along the X-ray center axis. In FIG. 8, reference numeral 32 denotes an X-ray center axis when performing a micro CT imaging operation.

Subsequently, the dual focus type X-ray source 36 irradiates an X-ray for micro CT imaging while rotating the rotary table 28 by the rotary table drive unit 29. Then, the common X-ray detector 21 detects the X-ray transmitted through an object and transmits a detection signal to the computer.

When performing a general CT imaging operation, as shown in FIG. 9, the rotary arm drive unit 24 is moved in front-rear and left-right directions so that the center of the rotary arm drive unit 24 coincides with the center of the body portion of the patient to be imaged. In FIG. 9, reference numeral 33 denotes an X-ray center axis when performing a general CT imaging operation.

In this state, the head of the patient is positioned on the jaw fixing portion of the patient support arm 30. Then, the X-ray for general CT imaging is emitted from the dual X-ray source 36 while allowing the horizontal rotation arm 23 to rotate 360 degrees around the head of the patient. The common X-ray detector 21 detects the X-ray transmitted through a part of the human body and transmits a detection signal to the computer.

Other matters are the same as those of the first embodiment described above.

The embodiments described above are presented to merely describe preferred embodiments of the present invention. The scope of the present invention is not limited to the above-described embodiments. Those skilled in the art may make various changes, modifications or substitutions within the spirit of the present invention and the claims. It is to be understood that such changes, modifications or substitutions fall within the scope of the present invention.

What is claimed is:

1. An X-ray computed tomography apparatus with a scanner function, comprising:
    a vertical frame;
    a patient support arm provided below the vertical frame;
    a horizontal support arm extending horizontally from a top portion of the vertical frame;
    a rotary arm drive unit provided at an end of the horizontal support arm;
    a horizontal rotation arm provided horizontally below the rotary arm drive unit to rotate 360 degrees;
    a general CT imaging X-ray source provided at one end of the horizontal rotation arm; and
    an X-ray detector provided at the other end of the horizontal rotation arm to face the general CT imaging X-ray source,
    wherein a micro CT imaging X-ray source is further provided on the vertical frame, a rotary table for seating and rotating an object to be imaged is further provided above the patient support arm, and the X-ray detector is composed of a common X-ray detector configured to be rotated by an X-ray detector drive unit, so that the apparatus performs both a micro CT imaging operation and a general CT imaging operation.

2. The apparatus according to claim 1, wherein a rotary table drive unit for rotating the rotary table is provided below the rotary table.

3. The apparatus according to claim 2, wherein the rotary table drive unit is provided so as to be movable along a rail provided on the patient support arm.

4. The apparatus according to claim 2, wherein the rotary table or the rotary table drive unit is detachably provided on an upper surface of the patient support arm.

5. The apparatus according to claim 1, wherein the micro CT imaging X-ray source is provided to be able to move up and down and rotate at a predetermined angle in a horizontal direction.

6. The apparatus according to claim 1, wherein when performing the micro CT imaging operation, the micro CT imaging X-ray source and the common X-ray detector are rotated at a predetermined angle, the centers of the micro CT imaging X-ray source and the rotary table are placed on a line, and then the micro CT imaging X-ray source and the common X-ray detector are allowed to face each other.

7. The apparatus according to claim 1, wherein a first X-ray source and a second X-ray source for performing the micro CT imaging operation by irradiating X-rays having different focuses are provided on the vertical frame.

8. An X-ray computed tomography apparatus with a scanner function, comprising:
    a vertical frame;
    a patient support arm provided below the vertical frame;
    a horizontal support arm extending horizontally from a top portion of the vertical frame;
    a rotary arm drive unit provided at an end of the horizontal support arm;
    a horizontal rotation arm provided horizontally below the rotary arm drive unit to rotate 360 degrees;
    an X-ray source provided at one end of the horizontal rotation arm; and
    an X-ray detector provided at the other end of the horizontal rotation arm to face the X-ray source,
    wherein the X-ray source is composed of a dual focus type X-ray source configured to emit both a micro CT imaging X-ray and a general CT imaging X-ray from one tube, so that the apparatus performs both a micro CT imaging operation and a general CT imaging operation.

9. The apparatus according to claim 8, wherein a rotary table drive unit for rotating the rotary table is provided below the rotary table.

10. The apparatus according to claim 9, wherein the rotary table drive unit is provided so as to be movable along a rail provided on the patient support arm.

11. The apparatus according to claim 9, wherein the rotary table or the rotary table drive unit is detachably provided on an upper surface of the patient support arm.

* * * * *